United States Patent [19]
Wright

[11] Patent Number: 6,081,922
[45] Date of Patent: Jul. 4, 2000

[54] SUN VISOR

[76] Inventor: Wilbert L. Wright, 1371 NW. 98 Ter., Miami, Fla. 33147

[21] Appl. No.: 09/244,393

[22] Filed: Feb. 4, 1999

[51] Int. Cl.[7] ............................................... A61F 9/00

[52] U.S. Cl. ................................. 2/12; 2/200.3; 2/209.11

[58] Field of Search ................................. 2/10, 12, 200.3, 2/209.11

[56] References Cited

U.S. PATENT DOCUMENTS

| 1,673,859 | 6/1928 | Wittcoff | 2/10 |
| 5,406,645 | 4/1995 | Lin | 2/10 |

*Primary Examiner*—John J. Calvert
*Assistant Examiner*—Katherine Moran

[57] ABSTRACT

A sun visor for wear on the head of a user to shade the face, the ears, and back of the neck of the user. The sun visor includes a panel with a fold dividing the panel into front and back portions. The panel has a head hole therethrough.

14 Claims, 2 Drawing Sheets

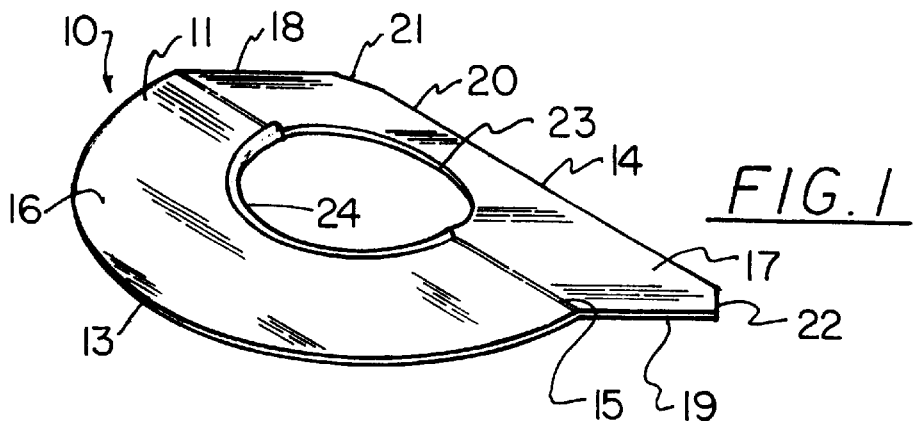
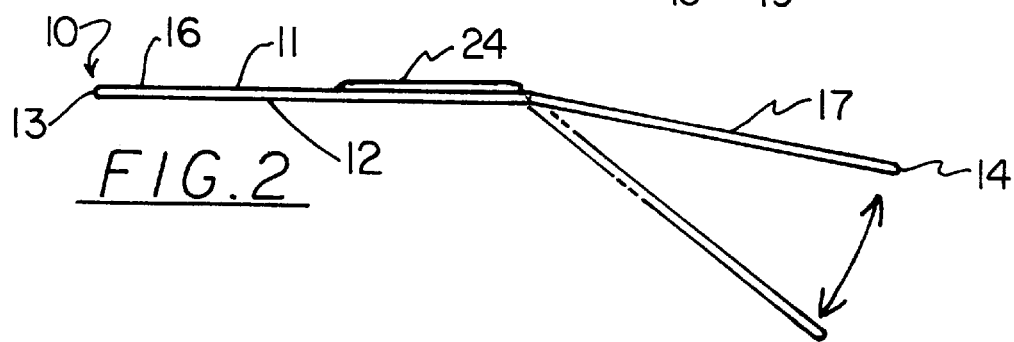
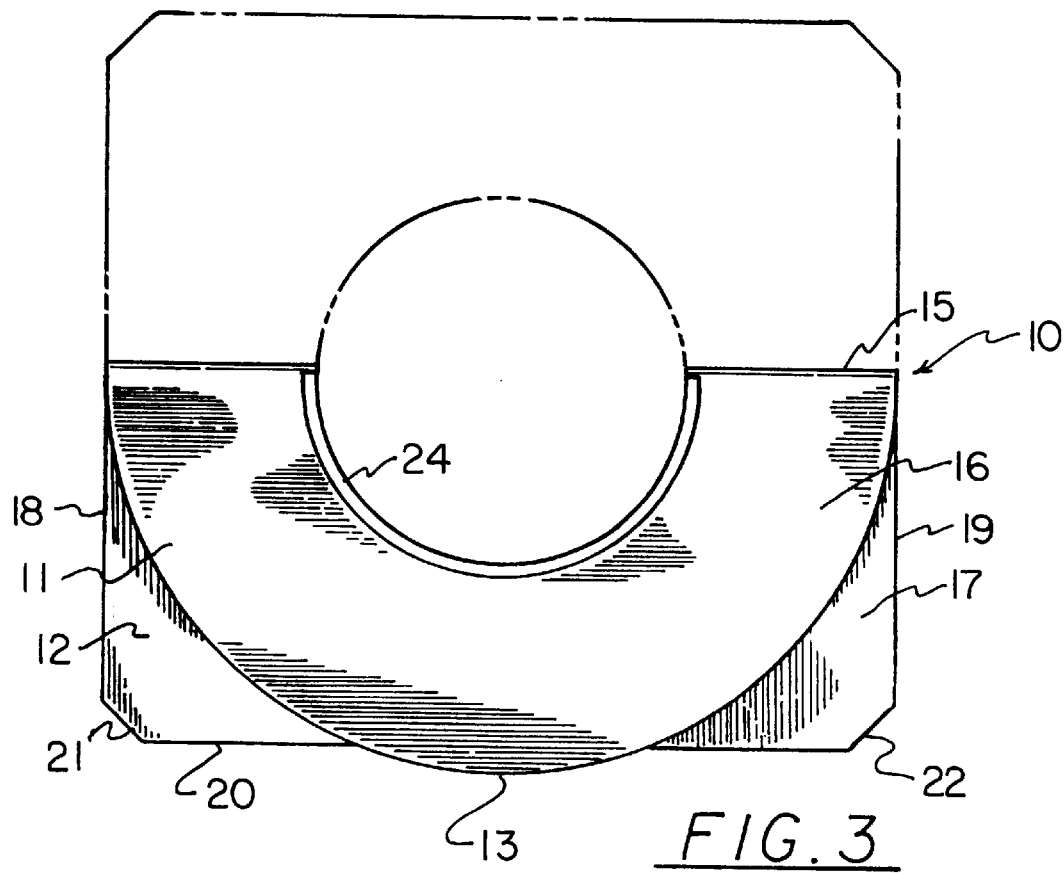

SUN VISOR

BACKGROUND OF THE INVENTION

1. Field of the Invention

The present invention relates to sun visors and more particularly pertains to a new sun visor for wear on the head of a user to shade the face, the ears, and back of the neck of the user.

2. Description of the Prior Art

The use of sun visors is known in the prior art. More specifically, sun visors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. Des. 255,395; U.S. Pat. No. 5,091,995; U.S. Pat. No. 5,323,491; U.S. Pat. No. 4,704,744; U.S. Pat. No. 3,235,882; and U.S. Pat. No. 2,446,053.

While these devices fulfill their respective, particular objectives and requirements, the aforementioned patents do not disclose a new sun visor. The inventive device includes a panel with a fold dividing the panel into front and back portions. The panel has a head hole therethrough.

In these respects, the sun visor according to the present invention substantially departs from the conventional concepts and designs of the prior art, and in so doing provides an apparatus primarily developed for the purpose of wear on the head of a user to shade the face, the ears, and back of the neck of the user.

SUMMARY OF THE INVENTION

In view of the foregoing disadvantages inherent in the known types of sun visors now present in the prior art, the present invention provides a new sun visor construction wherein the same can be utilized for wear on the head of a user to shade the face, the ears, and back of the neck of the user.

The general purpose of the present invention, which will be described subsequently in greater detail, is to provide a new sun visor apparatus and method which has many of the advantages of the sun visors mentioned heretofore and many novel features that result in a new sun visor which is not anticipated, rendered obvious, suggested, or even implied by any of the prior art sun visors, either alone or in any combination thereof.

To attain this, the present invention generally comprises a panel with a fold dividing the panel into front and back portions. The panel has a head hole therethrough.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new sun visor apparatus and method which has many of the advantages of the sun visors mentioned heretofore and many novel features that result in a new sun visor which is not anticipated, rendered obvious, suggested, or even implied by any of the prior art sun visors, either alone or in any combination thereof.

It is another object of the present invention to provide a new sun visor which may be easily and efficiently manufactured and marketed.

It is a further object of the present invention to provide a new sun visor which is of a durable and reliable construction.

An even further object of the present invention is to provide a new sun visor which is susceptible of a low cost of manufacture with regard to both materials and labor, and which accordingly is then susceptible of low prices of sale to the consuming public, thereby making such sun visor economically available to the buying public.

Still yet another object of the present invention is to provide a new sun visor which provides in the apparatuses and methods of the prior art some of the advantages thereof, while simultaneously overcoming some of the disadvantages normally associated therewith.

Still another object of the present invention is to provide a new sun visor for wear on the head of a user to shade the face, the ears, and back of the neck of the user.

Yet another object of the present invention is to provide a new sun visor which includes a panel with a fold dividing the panel into front and back portions. The panel has a head hole therethrough.

Still yet another object of the present invention is to provide a new sun visor that protects the portions of the head and neck from sunburn.

Even still another object of the present invention is to provide a new sun visor that is foldable for convenient storage when not in use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new sun visor according to the present invention.

FIG. 2 is a schematic side view of the present invention.

FIG. 3 is another schematic side view of the present invention in a folded position.

DESCRIPTION OF THE PREFERRED EMBODIMENT

Figure 4:
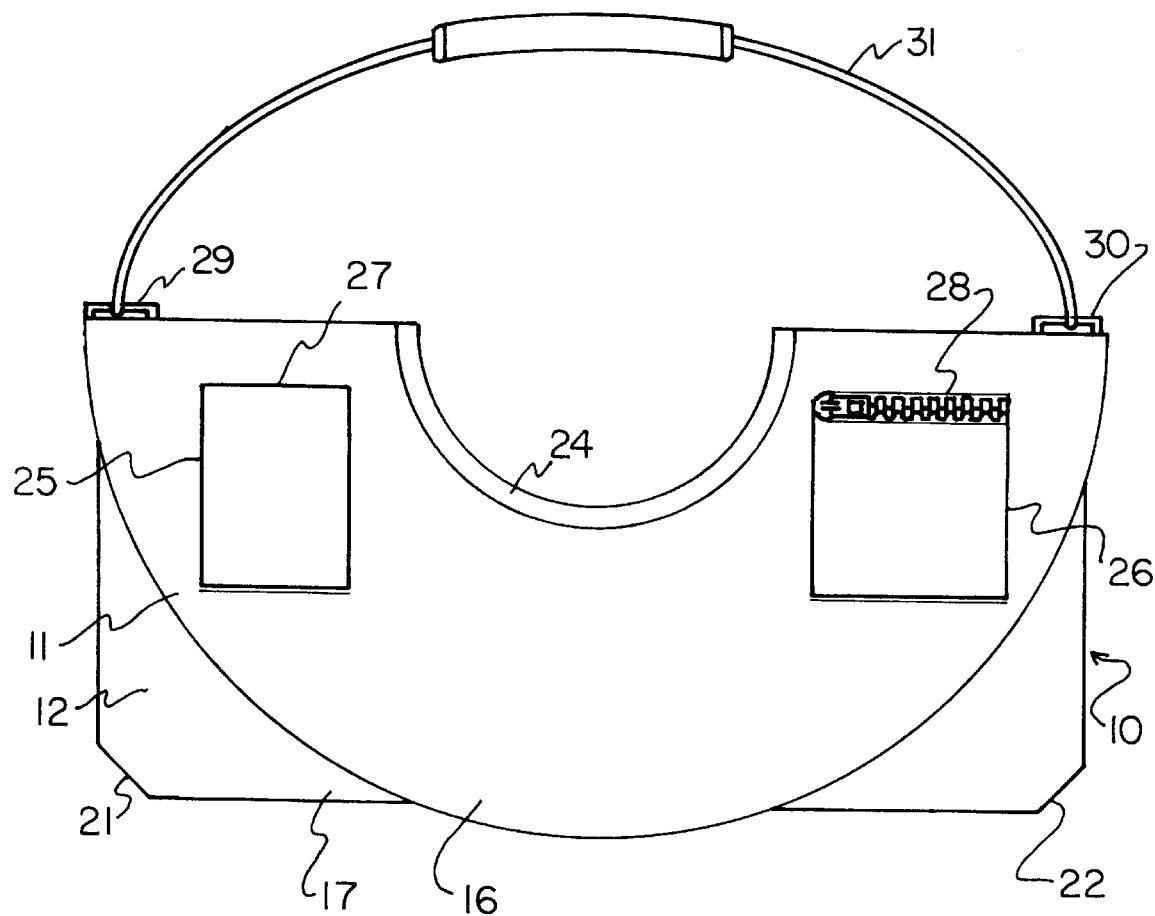
FIG. 4 is a schematic side view of a preferred embodiment of the present invention.

With reference now to the drawings, and in particular to FIGS. 1 through 3 thereof, a new sun visor embodying the principles and concepts of the present invention will be described.

As best illustrated in FIGS. 1 through 3, the sun visor generally comprises a panel 10 with a fold dividing the panel 10 into front and back portions 16,17. The panel 10 has a head hole 23 therethrough.

In closer detail, the sun visor is designed for wear on the head of a user and comprises a panel 10 having substantially flat first and second faces 11,12, a front 13 and a back 14. The panel 10 has a fold 15 dividing the panel 10 into front and back portions 16,17. The front portion 16 is located towards the front 13 of the panel and the back portion 17 is located towards the back 14 of the panel.

The front portion 16 has an arcuate outer perimeter with a concavity facing towards the back 14 of the panel. Ideally, the arcuate outer perimeter is generally semi-circular and has a center and a diameter. The back portion 17 has a generally rectangular outer perimeter has a pair of generally straight side edges 18,19 and a generally straight back edge 20 extending between the side edges 18,19. The back edge 20 is positioned towards the back 14 of the panel. The back edge 20 and the fold 15 are extended substantially parallel to one another. The side edges 18,19 are preferably extended substantially parallel to one another and substantially perpendicular to the back edge 20.

Preferably, the outer perimeter of the back portion 17 has a pair of beveled corners 21,22. One of the beveled corners is located at the intersection of adjacent the one of the side edges and the back edge and the other of the beveled corners is located at the intersection of adjacent the other of the side edges and the back edge. The beveled corners 21,22 each are extended at an acute angle to the back edge and the associated side edge. Ideally, the beveled corners 21,22 are extended at about a 45 degree angle to the back edge and the associated side edge.

The back portion 17 has a width defined between the side edges 18,19. Preferably, the width of the back portion 17 and the diameter of the front portion 16 are about equal to one another. Ideally, the width of the back portion 17 and the diameter of the front portion 16 are each about 14 inches to provide optimal shade coverage to the face, ears, and back of the neck of a user to adequately protectively shade these portions from the sun. The panel 10 has a length defined between the front 13 and back 14 of the panel. Preferably, the length of the panel 10 is greater than the diameter of the front portion 16. Ideally, the length of the panel 10 is about 17 inches. The back portion 17 has a length defined along the length of the panel 10 between the fold 15 and the back edge 20. Preferably, the length of the back portion 17 is greater than the width of the back portion 17. Ideally, length of the back portion 17 is about 10 inches to provide optimal shading to the back of the neck of the user.

The panel 10 has a generally circular head hole 23 therethrough between the first and second faces 11,12 of the panel. The head hole 23 has a center and a diameter and a generally circular outer periphery or circumference. The centers of the front portion 16 and the head hole 23 are preferably substantially coaxial with one another so that the head hole 23 is centered on the panel 10 and the fold 15 bisects the head hole 23. In use, the head hole 23 is designed for inserting the head of a user therethrough such that the outer periphery of the head hole 23 rests against the head of the user to hold the panel 10 on the head of the user above the face, ears, and back of the neck of the user.

An arcuate resiliently deformable padding strip 24 is preferably coupled to the outer periphery of the head hole 23. The padding strip 24 is preferably positioned along the outer periphery towards the front 13 of the panel. Ideally, the padding strip 24 comprises a resiliently deformnable foamed material for helping reduce the overall weight of the sun visor. The padding strip 24 is preferably generally semi-circular in shape and has a pair of opposite ends. Each of the ends of the padding strip 24 is positioned adjacent the fold 15. In use, the padding strip 24 is designed for abutting against the forehead of the user to help hold the panel 10 in a position on the head of the user and to help hold the panel 10 against rotation on the head of the user. As best illustrated in FIG. 2, the padding strip 24 has a portion outwardly extending from the first face 11 of the panel so that padding does not become detached from repeated wear from use every time the a head is inserted into the head hole 23 from the second face 12 of the panel.

In a preferred embodiment illustrated in FIG. 4, the first face 11 of the panel 10 has a plurality of pockets 25,26 for holding items to the first face 11 of the panel. The pockets 25,26 are preferably positioned on the front portion 16. Each of the pockets 25,26 has an opening 27 therein to permit insertion of items therein. Preferably, the openings 27 of the pockets 25,26 face the fold 15. Ideally, at least one of the pockets has a zipper 28 substantially closing the associated opening of the respective pocket.

With reference to FIG. 2, in use, the front and back portions 16,17 are pivotable with respective to one another along the fold 15. The front and back portions 16,17 are pivotable between an extended position and folded position. When the front and back portions 16,17 are in the extended position, the first face 11 and the second face 12 of the entire panel 10 may lie in parallel planes. As illustrated in FIGS. 3 and 4, the second face of the front portion faces the second face of the back portion when the front and back portions are in the folded position. The folded position is designed for convenient storage of the sun visor when not in use Ideally, as illustrated in FIG. 4, the first face 11 of the panel 10 has a pair of generally inverted rectangular U-shaped loops 29,30 outwardly extending therefrom. The loops 29,30 are preferably positioned along the fold 15. An adjustable length carrying strap 31 has a pair of opposite ends. One of the ends of the carrying strap is coupled or hooked to one of the loops and the other of the ends of the carrying strap is coupled or hooked to the other of the loops.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A sun visor, comprising:
   a panel having first and second faces, a front and a back;
   said panel having a fold dividing said panel into front and back portions, said front portion being located towards said front of said panel, said back portion being located towards said back of said panel;
   said panel having a head hole therethrough between said first and second faces of said panel;
   wherein said front portion has an arcuate outer perimeter, said arcuate outer perimeter of said front portion having a concavity facing towards said back of said panel, wherein said arcuate outer perimeter is generally semi-circular and has a center and a diameter; and
   wherein said back portion has a generally rectangular outer perimeter having a pair of generally straight side edges and a generally straight back edge extending between said side edges, said back edge being positioned towards said back of said panel, said back portion having a width defined between said side edges.

2. The sun visor of claim 1, wherein said width of said back portion and said diameter of said front portion are about equal to one another.

3. The sun visor of claim 1, wherein said back edge and said fold are extended substantially parallel to one another, and wherein said side edges are extended substantially parallel to one another and substantially perpendicular to said back edge.

4. The sun visor of claim 1, wherein said outer perimeter of said back portion has a pair of beveled corners, one of said beveled corners being located adjacent said one of said side edges and said back edge, the other of said beveled corners being located adjacent the other of said side edges and said back edge, said beveled corners each being extended at an acute angle to said back edge and the associated side edge.

5. The sun visor of claim 4, wherein said beveled corners are extended at about a 45 degree angle to said back edge and the associated side edge.

6. The sun visor of claim 1, wherein a deformable padding strip is coupled to said outer periphery of said head hole, said padding strip being positioned along said outer periphery towards said front of said panel.

7. The sun visor of claim 6, wherein said padding strip has a pair of opposite ends, each of said ends of said padding strip being positioned adjacent said fold.

8. The sun visor of claim 1, wherein said first face of said panel has a plurality of pockets.

9. The sun visor of claim 8, wherein each of said pockets has an opening, and wherein at least one of said pockets has a zipper substantially closing the associated opening of the respective pocket.

10. A sun visor, comprising:
    a panel having substantially flat first and second faces, a front and a back;
    said panel having a fold dividing said panel into front and back portions, said front portion being located towards said front of said panel, said back portion being located towards said back of said panel;
    said front portion having an arcuate outer perimeter, said arcuate outer perimeter of said front portion having a concavity facing towards said back of said panel;
    wherein said arcuate outer perimeter is generally semi-circular and has a center and a diameter;
    said back portion having a generally rectangular outer perimeter having a pair of generally straight side edges and a generally straight back edge extending between said side edges;
    said back edge being positioned towards said back of said panel;
    said back edge and said fold being extended substantially parallel to one another;
    said side edges being extended substantially parallel to one another and substantially perpendicular to said back edge;
    said outer perimeter of said back portion having a pair of beveled corners, one of said beveled corners being located adjacent said one of said side edges and said back edge, the other of said beveled corners being located adjacent the other of said side edges and said back edge;
    wherein said beveled corners are extended at about a 45 degree angle to said back edge and the associated side edge;
    said back portion having a width defined between said side edges;
    said width of said back portion and said diameter of said front portion are about equal to one another;
    said panel having a length defined between said front and back of said panel, wherein said length of said panel is greater than said diameter of said front portion;
    said back portion having a length defined between said fold and said back edge, wherein said length of said back portion is greater than said width of said back portion;
    said panel having a generally circular head hole therethrough between said first and second faces of said panel;
    said head hole having a center and a diameter and a generally circular outer periphery;
    said centers of said front portion and said head hole being substantially coaxial with one another;
    said head hole being adapted for inserting the head of a user therethrough;
    an arcuate resiliently deformable padding strip being coupled to said outer periphery of said head hole, said padding strip being positioned along said outer periphery towards said front of said panel;
    wherein said padding strip comprises a foamed material;
    said padding strip being generally semi-circular in shape and having a pair of opposite ends, each of said ends of said padding strip being positioned adjacent said fold;
    said padding strip being adapted for abutting against the forehead of the user to help hold the panel in a position on the head of the user;

said padding strip having a portion outwardly extending from said first face of said panel;

said first face of said panel having a plurality of pockets;

said pockets being positioned on said front portion;

each of said pockets having an opening;

wherein at least one of said pockets has a zipper substantially closing the associated opening of the respective pocket; and said front and back portions being pivotable with respective to one another along said fold.

11. A sun visor, comprising:

a panel having first and second faces, a front and a back;

said panel having a fold dividing said panel into front and back portions, said front portion being located towards said front of said panel, said back portion being located towards said back of said panel;

said panel having a head hole therethrough between said first and second faces of said panel; and wherein a deformable padding strip is coupled to said outer periphery of said head hole, said padding strip being positioned along said outer periphery towards said front of said panel.

12. The sun visor of claim 11, wherein said padding strip has a pair of opposite ends, each of said ends of said padding strip being positioned adjacent said fold.

13. The sun visor of claim 11, wherein said first face of said panel has a plurality of pockets.

14. The sun visor of claim 13, wherein each of said pockets has an opening, and wherein at least one of said pockets has a zipper substantially closing the associated opening of the respective pocket.

* * * * *